(12) United States Patent
Jaunzems

(10) Patent No.: US 9,458,084 B2
(45) Date of Patent: Oct. 4, 2016

(54) MANUFACTURE OF 1-SUBSTITUTED METHYLIDENE COMPOUNDS

(71) Applicant: SOLVAY SA, Brussels (BE)

(72) Inventor: Janis Jaunzems, Hannover (DE)

(73) Assignee: SOLVAY SA, Brussels (BE)

( * ) Notice: Subject to any disclaimer, the term of this patent is extended or adjusted under 35 U.S.C. 154(b) by 0 days.

(21) Appl. No.: 14/400,422

(22) PCT Filed: May 7, 2013

(86) PCT No.: PCT/EP2013/059526
§ 371 (c)(1),
(2) Date: Nov. 11, 2014

(87) PCT Pub. No.: WO2013/171102
PCT Pub. Date: Nov. 21, 2013

(65) Prior Publication Data
US 2015/0126765 A1    May 7, 2015

(51) Int. Cl.
*C07C 67/343* (2006.01)
*C07C 69/738* (2006.01)
*A01N 37/06* (2006.01)

(52) U.S. Cl.
CPC ............. *C07C 67/343* (2013.01); *A01N 37/06* (2013.01)

(58) Field of Classification Search
CPC .................................................. C07C 67/343
See application file for complete search history.

(56) References Cited

U.S. PATENT DOCUMENTS

| 7,521,397 B2 | 4/2009 | Dunkel et al. |
| 2011/0009642 A1 | 1/2011 | Pazenok |

FOREIGN PATENT DOCUMENTS

| CH | WO 2011113789 A1 * | 9/2011 | ........... C07C 67/343 |
| WO | 03070705 A1 | 8/2003 | |
| WO | 2011113789 A1 | 9/2011 | |
| WO | 2012010692 A1 | 1/2012 | |

* cited by examiner

*Primary Examiner* — Yong Chu

(57) ABSTRACT

The present disclosure relates to compounds of the formula

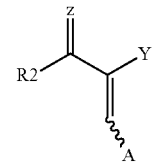

(I)

wherein $R^2$ and A are certain substituents, Y is an ester group, a nitrile group or an amido group and Z is O, S or $N^+R^2$, and which compounds are, for example, useful as intermediates for pyrazole fungicides. The compounds of the present disclosure can be prepared by the reaction of a compound of formula $R^2$—C(O)—$CH_2Y$, with an orthoformate HC—$(OR^3)_3$ in the presence of a base, especially in the presence of an amine, e.g. triethylamine.

14 Claims, No Drawings

MANUFACTURE OF 1-SUBSTITUTED METHYLIDENE COMPOUNDS

This application is a U.S. national stage entry under 35 U.S.C. §371 of International Application No. PCT/EP2013/059526 filed May 7, 2013, which claims priority to European application No. EP 12168163.9 filed on 16 May 2012. The entire contents of these applications are explicitly incorporated herein by this reference.

The present invention concerns a method for the manufacture of 1-substituted methylidene compounds.

1-substituted pyrazoles, e.g. 1-alkylpyrazoles, as is described in US 2011/000962, are intermediates for fungicides.

Intermediates which can be used to provide such fungicides are compounds having the formula

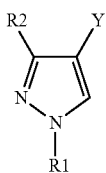

In which $R^1$ and $R^2$ are certain organic substituents and Y is an ester group, a nitrile group or an amido group.

Compounds of formula (I) can be manufactured in a process which comprises several steps. For example, a compound of formula $R^2$—C(O)—CH$_2$Y is reacted with an orthoformate in the presence of a molar excess of an anhydride of a carboxylic acid, e.g. in the presence of acetic acid anhydride, to provide an intermediate alkoxymethylidene compound which in turn is reacted with a monosubstituted hydrazine to form the compound of formula (I). This is described on page 11 of WO 2012/010692. The use of an excess of an anhydride of a carboxylic acid in the reaction between the compound of formula $R^2$—C(O)CH$_2$Y and the orthoformate provides a lot of waste.

Object of the present invention is to provide an improved process to provide methylidene compounds useful for the manufacture of pyrazoles.

The present invention provides a method for the manufacture of a compound of formula (I)

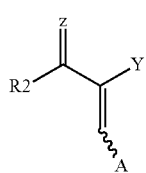

(I)

by the reaction of a compound of formula (II), $R^2$—C(O)—CH$_2$Y, with an orthoformate of formula (III), HC—(OR$^3$)$_3$ in the presence of a base wherein $R^2$ is selected from C1 to C4 alkyl groups are substituted by one, two or three halogen atoms selected from the group consisting of F, Cl and Br or a CF$_3$ group;

$R^3$ is C1 to C8 alkyl; C3 to C8 cycloalkyl; C2 to C8 alkenyl; benzyl or phenyl; C1 to C8 alkyl, C3 to C8 cycloalkyl, C2 to C8 alkenyl, benzyl or phenyl substituted by one or more groups selected from the group consisting of R', X, OR', SR', NR'$_2$, SiR'$_3$, COOR', C(O)R', CN and CONR'$_2$ wherein R' is H or a C1 to C12 group, and X is fluorine, chlorine, bromine and iodine, preferably fluorine or chlorine;

Y is selected from the group consisting of C(O)OR$^4$, CN and C(O)NR$^5$R$^6$ wherein R$^4$, R$^5$ and R$^6$ are independently of each other are selected from the group consisting of C1 to C12 alkyl; C3 to C8 cycloalkyl; C2 to C12 alkenyl; C2 to C12 alkynyl; C6 to C8 aryl; C7 to C19 arylalkyl; and C7 to C19 alkylaryl; each of which may be substituted by one or more groups selected from the group consisting of R', X, OR', SR', NR'$_2$, SiR'$_3$, COOR', C(O)R', CN and CONR'$_2$ wherein R' is H or a C1 to C12 group; and R$^5$ and R$^6$ together with the nitrogen atom to which they are attached may form a 5-membered or 6-membered ring which may optionally contain one or more further heteroatoms selected from the group consisting of O, S and an SO$_2$ group and which may be substituted by one or more groups selected from the group consisting of R', X, OR', SR', NR'$_2$, SiR'$_3$, COOR', C(O)R', CN and CONR'$_2$ wherein R' is H or a C1 to C12 group; and X is fluorine, chlorine, bromine and iodine, preferably fluorine or chlorine;

A is OR$^3$ wherein R$^3$ has the meaning given above;

Z is selected from the group consisting of O, S and N$^+$R$^7$R$^8$ wherein R$^7$ and R$^8$ independently from each other are selected from the group consisting of C1 to C12 alkyl; C3 to C8 cycloalkyl; C2 to C12 alkenyl; C2 to C12 alkynyl; C6 to C8 aryl; C7 to C19 arylalkyl; and C7 to C19 alkylaryl; each of which may be substituted by one or more groups selected from the group consisting of R', X, OR', SR', NR'$_2$, SiR'$_3$, COOR', C(O)R', CN and CONR'$_2$ wherein R' is H or a C1 to C12 group; and R$^7$ and R$^8$ together with the nitrogen atom to which they are attached may form a 5-membered or 6-membered ring which may optionally contain one or more further heteroatoms selected from the group consisting of O, S and an SO$_2$ group and which may be substituted by one or more groups selected from the group consisting of R', X, OR', SR', NR'$_2$, SiR'$_3$, COOR', C(O)R', CN and CONR'$_2$ wherein R' is H or a C1 to C12 group; and X is fluorine, chlorine, bromine and iodine, preferably fluorine or chlorine; and when Z is N$^+$R$^7$R$^8$ the positive charge is balanced by an anion, e.g. by a sulfate anion or Cl$^-$.

$R^1$ preferably is C1 to C5 alkyl; or C1 to C5 alkyl, substituted by at least one halogen atom, and more preferably, $R^1$ is methyl, ethyl, n-propyl, i-propyl, n-butyl, s-butyl, t-butyl or n-pentyl. Especially preferably, $R^1$ is methyl or ethyl, most preferably, methyl.

Preferably, in the context of the present invention, $R^2$ is chloromethyl, dichloromethyl, trichloromethyl, fluoromethyl, difluoromethyl, trifluoromethyl, chlorobromomethyl, chlorofluoromethyl, chlorodifluoromethyl, fluorodichloromethyl, 1-fluoroethyl, 2-fluoroethyl, 2,2-difluoroethyl, 2,2,2-trifluoroethyl, 1-chloroethyl, 2,2-dichloroethyl, 1,2-dichloroethyl, 2-chlorofluoroethyl, 2-chloro-2,2-difluoroethyl, 2,2-dichloro-2-fluoroethyl, 2,2,2-trichloroethyl, pentafluoroethyl and 1,1,1-trifluoro-prop-2-yl; especially preferably, $R^2$ is CH$_2$F, CHF$_2$, CClF$_2$ or CF$_3$. In many fungicidal pyrazoles, $R^2$ is CHF$_2$. Thus, in the frame of the present invention, $R^2$ is most preferably CClF$_2$ or CHF$_2$. If $R^2$ is CClF$_2$, it can be reduced to CHF$_2$ as described in WO 2012/010692 using hydrides, Zn/alcohol or H$_2$/catalyst, e.g. Pd.

Preferably, Z is O.

Preferably, Y is C(O)OR$^4$ wherein R$^4$ is a C1 to C5 alkyl group.

More preferably, $R^1$ is methyl or ethyl, $R^2$ is CHF$_2$, CClF$_2$ or CF$_3$, and $R^3$ is methyl or ethyl.

Preferably, R$^3$, R$^4$, R$^5$, R$^6$, R$^7$ and R$^8$ are methyl, ethyl, propyl or butyl, and especially, methyl or ethyl.

Especially preferably, $R^1$ is methyl, $R^2$ is $CHF_2$, $CClF_2$ or $CF_3$, and $R^3$ and $R^4$ are methyl or ethyl.

The base may be any inorganic or organic Brønstedt base.

Inorganic bases can for instance be selected from alkali metal phosphates, acetates, hydroxides, carbonates and hydrogen carbonates; for example, $K_2CO_3$, $Cs_2CO_3$, $Na_2CO_3$, $NaHCO_3$, $K_3PO_4$, NaOAc, NaOH, LiOH or KOH are useful inorganic bases.

Organic bases are preferred. Preferred organic bases comprise at least one 3-coordinated N atom.

For example, amines having the formula (IV), $NR^9R^{10}R^{11}$, are suitable.

According to one embodiment, $R^9$, $R^{10}$ and $R^{11}$ are the same or different and are H or C1 to C10 alkyl with the proviso that at least one of $R^9$, $R^{10}$ and $R^{11}$ is not H. Preferably, $R^9$, $R^{10}$ and $R^{11}$ are C1 to C3 alkyl; especially preferably, $R^9$, $R^{10}$ and $R^{11}$ are ethyl.

According to another embodiment, at least $R^9$ and $R^{10}$ form a saturated ring with 3 to 8 members; $R^{11}$ is H or C1 to C10 alkyl. The saturated ring may comprise one or more hetero atoms, selected from N, O and S. Examples are aziridine, pyrrolidine, piperidine, N-methylpyrolidine, N-methylpiperidine and piperazine, and morpholine. Examples for aromatic amines are, for example, imidazole, pyridine, pyrimidine, dimethylaminopyridine; but other aromatic amines may also be used.

According to still another embodiment, $R^9$ forms a saturated or unsaturated ring with 5 to 8 members; $R^{10}$ and $R^{11}$ are H or C1 to C10 alkyl. Examples are cyclohexylamine, aniline and methylaniline.

According to another embodiment, $R^9$, $R^{10}$ and $R^{11}$ form a cyclic system. Examples are 1,5-diazabicyclo[4.3.0]non-5-ene (DBN) and 1,8-diazabicyclo[5.4.0]undec-7-ene (DBU).

Trialkylamines wherein $R^9$, $R^{10}$ and $R^{11}$ are C1 to C4 alkyl, more preferably, C1 to C3 alkyl, and most preferably are methyl or ethyl, are especially preferred.

The base, especially the amine, is preferably applied in catalytically amounts. Preferably, the molar ratio between the base, especially the amine, and the compound of formula (II) is equal to or greater than 0.001:1. Preferably, it is equal to or lower than 0.1:1. A preferred range for the molar ratio of base and the compound of formula (II) is from 0.001:1 to 0.1:1, and more preferably, it is from 0.001:1 to 0.05:1.

The reaction between the compound of formula (II) and (III) is performed at a temperature which allows for a reasonably fast reaction. Preferably, the temperature is equal to or greater than 80° C. More preferably, it is equal to or greater than 90° C. Especially preferably, it is equal to or greater than 100° C.

The upper limit of the reaction temperature is selected such that no undesired amounts of side reactions take place. Often, the reaction is performed at a temperature equal to or lower than 180° C., preferably, equal to or lower than 160° C.

If desired, the reaction between compounds of formula (II) and (III) can be performed in the presence of one or more high boiling solvents, for example, in the presence of at least one solvent selected from the group consisting of aprotic organic solvents. According to a preferred embodiment, an excess of the compound of formula (III) is applied as solvent. Triethylorthoformate is the preferred compound of formula (III), and thus, it is the especially preferred solvent.

In said reaction between the compounds of formulae (II) and (III), an alcohol $R^3OH$ is formed. The alcohol is generally removed from the reaction equilibrium by distillation. The alcohol is often very pure and must not be dumped, can be used as such, e.g. in chemical processes as reactant or solvent.

The reaction can be performed under ambient pressure, in a vacuum or at a pressure higher than ambient pressure. Since, as mentioned above, an alcohol $R^3OH$ is removed from the reaction, the reaction preferably is performed at ambient pressure or under applying a vacuum.

If desired, the reaction can be performed in the presence of an inert gas, e.g. in the presence of $N_2$.

The reaction temperature generally is selected such that the reaction is performed reasonably fast with low side reactions, if any. It may be dependent from the starting materials and the base used. Preferably, the reaction temperature is equal to or higher than 80° C. Preferably, it is equal to or lower than 180° C. A preferred range for the reaction temperature is from 80 to 150° C.

The reaction time may be dependent from the reaction temperature, the starting materials and the base used. It may range from 1 minute to 5 hours. Often, it will be from 30 minutes to 3 hours.

If desired, the working up of the resulting reaction mixture can be performed according to methods known in the art. For example, solvent can be evaporated off, and the desired compound of formula (I) can be isolated and purified by distillation under a vacuum. But due to the high purity of the product after solvent removal, an additional step of purification is not necessary.

The compounds of formula (I) can be reacted, for example, as is described in WO 2012/010692, with mono-substituted hydrazines under cyclization to form the pyrazoles having the formula

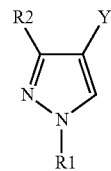

Wherein $R^1$, $R^2$ and Y have the meaning given above. Such pyrazoles are precursors of fungicidal active compounds; see for example, US 2011/0009642 and WO 03/070705. Often, in fungicides, the 3-halo group is $CHF_2$. Thus, if a pyrazole compound is produced having a $CClF_2$ group, this group can be reduced to form a difluoromethyl group. The reduction can be performed as described in WO 2012010692 using metal hydrides, $H_2$/catalyst (e.g. $H_2$/Pd) or metal/hydrogen source, e.g. Zn/ethanol.

The advantages of the method of the invention are, i.a., a lower energy consumption because the reaction between the ester and the orthoformate can be performed at a lower temperature and with a faster reaction rate, no waste production because no acetic acid anhydride (or any other anhydride) is necessary, nearly one equivalent of triethylorthoformate is consumed, and the yield is near quantitative and the purity of the product is exceptional.

Should the disclosure of any patents, patent applications, and publications which are incorporated herein by reference conflict with the description of the present application to the extent that it may render a term unclear, the present description shall take precedence.

The following examples are intended to explain the invention in further detail without the intention to limit it.

General Remarks:

Triethylorthoformate (TEOF) is commercially available. Ethyl difluorochloroacetate (ECDFAA) is commercially available from Solvay Fluor GmbH, Hannover/Deutschland.

EXAMPLE 1

Manufacture of 4-chloro-2-[1-ethoxy-meth-(Z)-ylidene]-4,4-difluoro-3-oxo-butyric acid ethyl Ester ("EME-CDFAA")

Triethylorthoformate (37 g=0.25 mol), ECDFAA (10 g=50 mmol) and triethylamine (15.6 mg=0.15 mmol) were given into a flask equipped with a Liebig condenser suitable for vacuum distillation. The resulting mixture was heated to 110° C. The pressure was lowered to 300 mbar, and ethanol formed was distilled off. After 3 hours, the ECDFAA was completely consumed and converted to the desired EME-CDFAA, and any remaining ethanol was evaporated off. The resulting mixture was then brought to 100° C., and the pressure was lowered slowly from 300 mbar to 10 mbar to distill off any excess of the triethyl orthoformate. 12.2 g of an amber-yellow oil with a purity of 99% (determined by gas chromatography) remained in the flask. The raw product could be used immediately without further purification for the next reaction step.

$^1$H NMR (500 MHz, CHLOROFORM-d), δ ppm (the spectrum shows a ratio of E to Z compound of 1:2):1.25-1.35 (4 t, 6H); 4.20-4.38 (4 q, 4H) and 7.76 (bs, 1H).

EXAMPLE 2

Comparison Example

Manufacture of 4-chloro-2-[1-ethoxy-meth-(Z)-ylidene]-4,4-difluoro-3-oxo-butyric acid ethyl Ester ("EME-CDFAA") using acetic acid anhydride Triethylorthoformate (415 g=2.15 mol), ECDFAA (280 g=1.4 mol) and acetic acid anhydride (428 g=4.2 mol) were given into a flask equipped with a vacuum distillation cooler. The resulting mixture was heated to 135° C. (outer temperature. Slowly, formed light boilers were distilled off. After 9 hours, the mixture was heated to 110° C. under slowly lowering the pressure from ambient pressure to a vacuum of 10 mbar; all light boilers were distilled out of the reaction mixture. A yellow-brown liquid with a purity of 87% (determined by gas chromatography) remained in the flask. The raw product could be used immediately without further purification for the next reaction step.

$^1$H NMR (500 MHz, CHLOROFORM-d), δ ppm (the spectrum shows a ratio of E to Z compound of 1:2.5): 1.25-1.35 (4 t, 6H); 4.20-4.38 (4 q, 4H) and 7.76 (bs, 1H).

The invention claimed is:

1. A method for the manufacture of a compound of formula (I)

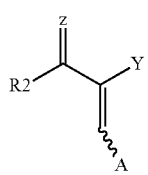

(I)

the method comprising: reacting a compound of formula (II), $R^2$—C(O)—$CH_2$Y, with an orthoformate of formula (III), HC—$(OR^3)_3$ in the presence of a base wherein $R^2$ is selected from C1 to C4 alkyl groups are substituted by one, two or three halogen atoms selected from the group consisting of F, Cl and Br or a $CF_3$ group;

$R^3$ is C1 to C8 alkyl; C3 to C8 cycloalkyl; C2 to C8 alkenyl; benzyl or phenyl; C1 to C8 alkyl, C3 to C8 cycloalkyl, C2 to C8 alkenyl, benzyl or phenyl substituted by one or more groups selected from the group consisting of R', X, OR', SR', $NR'_2$, $SiR'_3$, COOR', C(O)R', CN and $CONR'_2$ wherein R' is H or a C1 to C12 group, and X is fluorine, chlorine, bromine and iodine;

Y is selected from the group consisting of C(O)$OR^4$, CN and C(O)$NR^5R^6$ wherein $R^4$, $R^5$ and $R^6$ are independently of each other are selected from the group consisting of C1 to C12 alkyl; C3 to C8 cycloalkyl; C2 to C12 alkenyl; C2 to C12 alkynyl; C6 to C8 aryl; C7 to C19 arylalkyl; and C7 to C19 alkylaryl; each of which may be substituted by one or more groups selected from the group consisting of R', X, OR', SR', $NR'_2$, $SiR'_3$, COOR', C(O)R', CN and $CONR'_2$ wherein R' is H or a C1 to C12 group; and $R^5$ and $R^6$ together with the nitrogen atom to which they are attached may form a 5-membered or 6-membered ring which may optionally contain one or more further heteroatoms selected from the group consisting of O, S and an $SO_2$ group and which may be substituted by one or more groups selected from the group consisting of R', X, OR', SR', $NR'_2$, $SiR'_3$, COOR', C(O)R', CN and $CONR'_2$ wherein R' is H or a C1 to C12 group; and X is fluorine, chlorine, bromine and iodine;

A is $OR^3$ wherein $R^3$ has the meaning given above;

Z is O.

2. The method of claim 1 wherein Y is C(O)$OR^3$ wherein $R^3$ is a C1 to C5 alkyl group.

3. The method of claim 1 wherein $R^2$ is selected from the group consisting of chloromethyl, dichloromethyl, trichloromethyl, fluoromethyl, difluoromethyl, trifluoromethyl, chlorobromomethyl, chlorofluoromethyl, chlorodifluoromethyl, fluorodichloromethyl, 1-fluoroethyl, 2-fluoroethyl, 2,2-difluoroethyl, 2,2,2-trifluoroethyl, 1-chloroethyl, 2,2-dichloroethyl, 1,2-dichloroethyl, 2-chlorofluoroethyl, 2-chloro-2,2-difluoroethyl, 2,2-dichloro-2-fluoroethyl, 2,2,2-trichloroethyl, pentafluoroethyl and 1,1,1-trifluoro-prop-2-yl.

4. The method of claim 1 wherein $R^2$ is $CClF_2$.

5. The method of claim 1 wherein $R^3$, $R^4$, $R^5$, $R^6$, $R^7$ and $R^8$ are C1 to C5 alkyl.

6. The method of claim 1 wherein the base is $NH_3$ or an organic base.

7. The method of claim 6 wherein the organic base is selected from primary, secondary and tertiary amines.

8. The method of claim 1 wherein the base is selected from amines having the formula (IV), $NR^9R^{10}R^{11}$, wherein $R^9$, $R^{10}$ and $R^{11}$ are the same or different and are H or C1 to C10 alkyl with the proviso that at least one of $R^9$, $R^{10}$ and $R^{11}$ is not H; or wherein at least $R^9$ and $R^{10}$ form a saturated ring with 3 to 8 members which optionally may contain one or more hetero atoms selected from the group consisting of N, O and S, and $R^{11}$ is H or C1 to C10 alkyl; or wherein $R^9$ forms a saturated or unsaturated ring with 5 to 8 members; $R^{10}$ and $R^{11}$ are H or C1 to C10 alkyl.

9. The method of claim 8 wherein $R^9$, $R^{10}$ and $R^{11}$ are C1 to C3 alkyl.

10. The method of claim 9 wherein $R^9$, $R^{10}$ and $R^{11}$ are ethyl.

11. The method of claim 1 wherein the molar ratio of base and the compound of formula (II) is from 0.001:1 to 0.1:1.

12. The method of claim 1 wherein the reaction temperature is from 80 to 150° C.

13. A process for the manufacture of a pyrazole having the structure

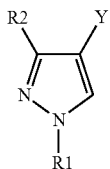

wherein
R¹ is C1 to C5 alkyl;
R² is selected from C1 to C4 alkyl groups are substituted by one, two or three halogen atoms selected from the group consisting of F, Cl and Br or a CF₃ group;
Y is selected from the group consisting of C(O)OR⁴, CN and C(O)NR⁵R⁶ wherein R⁴, R⁵ and R⁶ are independently of each other are selected from the group consisting of C1 to C12 alkyl; C3 to C8 cycloalkyl; C2 to C12 alkenyl; C2 to C12 alkynyl; C6 to C8 aryl; C7 to C19 arylalkyl; and C7 to C19 alkylaryl; each of which may be substituted by one or more groups selected from the group consisting of R', X, OR', SR', NR'₂, SiR'₃, COOR', C(O)R', CN and CONR'₂ wherein R' is H or a C1 to C12 group; and R⁵ and R⁶ together with the nitrogen atom to which they are attached may form a 5-membered or 6-membered ring which may optionally contain one or more further heteroatoms selected from the group consisting of O, S and an SO₂ group and which may be substituted by one or more groups selected from the group consisting of R', X, OR', SR', NR'₂, SiR'₃, COOR', C(O)R', CN and CONR'₂ wherein R' is H or a C1 to C12 group; and X is fluorine, chlorine, bromine and iodine;
the process comprising:
a) preparing a compound of formula (I) according to the process of claim 1, and
b) reacting the compound of formula (I) obtained in step (a) with a monosubstituted hydrazine having substituent R1, wherein R1 is defined above.

14. The process according to claim 13, wherein the agriculturally and/or pharmaceutically active compound pyrazole is an intermediate for a fungicide.

* * * * *